United States Patent [19]
Fleury et al.

[11] Patent Number: 5,463,894
[45] Date of Patent: Nov. 7, 1995

[54] PROCESS AND DEVICE FOR SURVEYING THE PROPERTIES OF A PERMEABLE MATERIAL

[75] Inventors: Marc Fleury, La Celle St Cloud; Roland Lenormand, Rueil Malmaison; Gabriel Ringot, Courbevoie, all of France

[73] Assignee: Institut Francais du Petrole, Rueil Malmaisson, France

[21] Appl. No.: 166,967

[22] Filed: Dec. 15, 1993

[30] Foreign Application Priority Data

Dec. 15, 1992 [FR] France .................... 92 15215

[51] Int. Cl.⁶ .................................. G01N 15/08
[52] U.S. Cl. ................................... 73/38
[58] Field of Search ........................ 73/38, 153

[56] References Cited

U.S. PATENT DOCUMENTS

| | | | |
|---|---|---|---|
| 4,679,422 | 7/1987 | Rubin et al. | 73/38 |
| 4,740,077 | 4/1988 | Goodwill | 73/38 |
| 4,868,751 | 9/1989 | Dogru et al. | 73/38 |
| 4,907,448 | 3/1990 | Givens | 73/153 |
| 5,069,065 | 12/1991 | Sprunt et al. | 73/153 |
| 5,079,948 | 1/1992 | Collins et al. | 73/153 |

FOREIGN PATENT DOCUMENTS

| | | |
|---|---|---|
| 0206372 | 12/1986 | European Pat. Off. . |
| 0473500 | 3/1992 | European Pat. Off. . |

OTHER PUBLICATIONS

AIME Translations vol. 160, 1945, pp. 114–123; G. L. Hassler, et al "Measurement of Capillary Pressures in Small Core Samples"; Abstract; FIG. 3.

*Primary Examiner*—Hezron E. Williams
*Assistant Examiner*—Michael J. Brock
*Attorney, Agent, or Firm*—Antonelli, Terry, Stout & Kraus

[57] ABSTRACT

The process mainly consists in placing a sample previously imbibed with a first fluid into a vessel or bucket containing another fluid of different density and in applying a centrifugal force by rotating the bucket at the end of an arm, so as to study the displacements of the fluids in the sample during at least two distinct phases. During the first phase, the rotational speed is increased so as to drain the first fluid from the sample. During the second phase, the rotational speed is progressively decreased. In order to avoid a discontinuity and to allow an imbibition of the sample, it is important to keep the two fluids in permanent contact with the sample. The amount of fluid produced in the bucket by centrifugation may be determined. The fluid produced may also be transferred into a variable chamber, for example inside the same bucket or a second rotating bucket.

19 Claims, 6 Drawing Sheets

FIG.4

PROCESS AND DEVICE FOR SURVEYING THE PROPERTIES OF A PERMEABLE MATERIAL

FIELD OF THE INVENTION

The object of the present invention is to propose an improved process and device for surveying the properties of a porous or permeable material.

More particularly, the invention relates to the measurement of the relative permeability of a material containing a fluid by subjecting it successively to one or several cycles including a draining phase and a imbibition phase.

BACKGROUND OF THE INVENTION

The process and the device may be applied to many fields, notably to the survey of oil-bearing reservoirs. The evaluation of the wealth and of the productivity of a subsurface reservoir is achieved for example by numerical simulations from the measured values of some parameters of the rocks such as the capillary pressure and the relative permeability thereof for the fluids present therein. These parameters are generally measured in a laboratory from rock samples taken in situ by coring.

One method for measuring the capillary pressure consists for example in subjecting porous rocks saturated with liquid to a progressive-speed centrifugation and in measuring the amount of fluid produced as a function of the speed.

A conventional method is known for taking measurements on a saturated sample successively in a draining phase and in an imbibition phase. The sample, previously saturated with a determined fluid, is placed in an enclosure, on a porous plate letting through only the fluid, and another fluid under pressure is injected so as to expel progressively the initial fluid. The fluid expelled from the sample is collected on the other side of the porous plate. During an imbibition phase, the centrifugal pressure is decreased so as to survey the return of the initial fluid in the sample.

French Patent application FR-2,666,147 (U.S. Pat. No. 5,253,529) mentions a known centrifuging system adapted for receiving a sample of a porous material containing a fluid (water for example). This centrifuging system includes a motor driving several arms into rotation. The samples, in the shape of cylindric bars possibly sheathed on the circumference thereof, are placed in buckets containing another fluid such as oil for example, respectively arranged at the end of the arms so that the centrifugal force draws the denser fluid away radially from the samples. The radial progression of the fluids inside the bar is determined by measuring the variations in the time of propagation of acoustic waves through the bar as the fluids move. Several couples of transducers transmitting and receiving ultrasounds are arranged opposite each other in various places along each bucket. The drained fluids flow into a free cavity provided in the peripheral part of the bucket.

With the device described in the above-cited patent, the phenomenon of expulsion of a fluid from a porous rock as the centrifugal force increases may be easily determined. But the inverse phenomenon of spontaneous imbibition of a core sample by the fluid previously drained, which may provide additional data on the material, cannot be observed because there is generally no more contact between the sample and the interface between the two fluids, and the denser fluid can therefore not re-imbibe it during the deceleration phase.

SUMMARY OF THE INVENTION

The process according to the invention allows the drawbacks mentioned above to be avoided and perfectly reproducible results to be obtained. It comprises applying a centrifugal force to a permeable or porous sample containing at least two fluids of different densities, with a phase of growth of the force up to a maximum value, then a phase of decrease, and measuring the displacement of the fluids outside the sample according to the intensity of the centrifugal force applied.

The process comprises keeping the sample in contact with the two fluids at least during the phase of decrease of the centrifugal force, so as to measure the displacement at least of the denser fluid re-entering the sample as a function of said centrifugal force.

The process comprises for example the follow-up of the interface between the two fluids outside the sample during the phase of growth and of decrease, or the stabilization thereof at a set level passing inside the sample volume at the level of an outer face of the sample for example. When the sample has the shape of a bar arranged parallel to the direction of the centrifugal force, said interface may be stabilized at an intermediate level between the two opposite faces, for example at the level of an outer face through which the denser fluid is expelled by the centrifugal force.

The process comprises for example placing a permeable or porous sample containing at least the two fluids of different densities into a vessel provided with a cavity for collecting the expelled fluid, rotating the vessel around an axis of rotation and keeping in the cavity the interface between the fluids (outside the sample) substantially in contact therewith and at least at the level of a face of the sample which is at the furthest distance from the axis of rotation by transfer of the fluids between the vessel and an auxiliary cavity.

Keeping the interface at the level of this face or at the set level comprises for example determining this level by acoustic telemetry, electric conductivity or pressure measurements.

The invention further relates to an implementing device including at least one vessel or bucket provided with an inner cavity for a sample in contact with the two fluids of different densities, the vessel being pivotably mounted to the end of a first arm integral with a axle, motor means for driving the arm in rotation and generating a centrifugal force, means for following up the displacements of the two fluids inside the sample.

The device comprises a variable-volume auxiliary chamber communicating with the vessel, means for determining the position of the interface between the fluid expelled by the centrifugal force and the other fluid (outside the sample) and a piloting assembly for controlling fluid transfers between said vessel and said auxiliary chamber so as to stabilize said interface and to avoid a loss of contact between the fluids and the sample.

The device includes for example a second vessel fastened to the end of an arm integral with the same axle, a piston adapted for tightly sliding into the second vessel and delimiting two variable-volume cavities, means for communicating the two cavities respectively with the opposite end parts of said first vessel and second motor means controlled by said piloting assembly, for moving the piston in the second vessel, thereby keeping the interface in contact with the sample.

According to another embodiment, the auxiliary chamber with the sliding piston can be disposed by the side of the inner cavity for the sample (within the same bucket or in another bucket) and communicate with the inner cavity the end parts thereof.

The means for following up the fluid displacements may include two sets of electroacoustic transducers distributed inside the vessel to determine the time of propagation of acoustic waves through said sample, and which are for example arranged on supporting rods associated with means for connection to the piloting system.

When one of the two fluids is electricity-conductive, the means for determining the location of the interface include for example conductive elements having each one end arranged at a different level close to said set level or to the contact level, these conductive elements being connected to an electric source. These conductive elements may also be arranged on a supporting rod associated with means for connection to the piloting system.

The means for determining the location of the interface (outside the sample) include for example acoustic echo-sounding elements for determining the variations in the interface level, or pressure detectors.

The device may also include two other arms arranged so as to balance the fulcrum pin, and provided each with a vessel, one of them including electroacoustic transducer means for achieving a temperature compensation allowing drifts likely to affect said set of transducers of the first vessel to be corrected.

The process according to the invention prevents any loss of contact between the two fluids and the sample. It allows a spontaneous imbibition of the sample which has been drained during a previous centrifuging phase to be achieved and therefore the reverse displacement of the interface between the two fluids to be observed during the following phase of decrease until it is cancelled out. Precise knowledge of the saturation in the sample and of the interface level outside the sample, which is permanently measured, allows the capillary pressure in the part of the bar between the interface and the face which is the closest to the axis of rotation to be determined.

Besides, when the interface between the two fluids is kept at a given set level and notably in contact with the base of the sample bar, the whole drainage-imbibition process may be observed continuously and the relative permeabilities may be determined with a constant limit position.

BRIEF DESCRIPTION OF THE DRAWINGS

Other features and advantages of the process and of the device according to the invention will be clear from reading the description hereafter of embodiments given by way of non limitative examples, with reference to the accompanying drawings in which:

FIGS. 2, 3 are diagrams illustrating the method according to the invention, FIG. 4 diagrammatically shows the lay-out of a centrifuging rotary support in an embodiment where the interface between the fluid is kept at a set level.

DESCRIPTION OF THE PREFERRED EMBODIMENTS

The tests relate for example to a sample having the shape of an elongated bar cut out of a porous material to be studied. The sample is saturated with a certain amount of a first fluid B, for example salt water. It is placed into a vessel which is filled with another fluid A, for example oil.

During a first draining stage, the assembly is then subjected to a centrifugal force directed along the length of the vessel so as to exert thereon a force of expulsion tending to flow out part of the first fluid B. At the same time, some fluid A flows into the sample. The two fluids move inside the sample until a position of equilibrium is reached, where the force due to the capillary pressure in the pores compensates the centrifugal force exerted. It is known that the capillary pressure $P_C$ is related to the distance r between the interface and the axis of rotation by the relation:

$$P_C = P_B - P_A = (\rho_B - \rho_A)^2 (r^2_{max} - r^2)$$

where ω is the angular rotation speed, $r_{max}$ is the distance between the base of the sample bar and the axis of rotation, $\rho_B$ and $\rho_A$ are the respective specific masses of fluids B and A.

The capillary pressure in the sample may be deduced from the precise measurement of the amount of initial fluid B extracted as a function of the centrifugal force exerted, and the variation in the average saturation $S_m$ of the sample with fluid B as a function of the centrifugal force exerted, which is obtained for example by acoustic detection as described in the French patent cited above.

With a sample saturated with a fluid B (initial $S_B = 100\%$), it may be seen (FIG. 1) that the saturation SBD during the centrifugal draining phase, for a determined radius r, decreases as the rotational speed increases until a minimum value $SB_{min}$ is reached. During this draining phase, the rotational speed is increased by successive steps until a speed of 3500 rpm for example is reached.

A deceleration phase is performed thereafter, where the speed is reduced by steps to zero.

If the drained fluid B is not in contact with the sample bar at the time of this deceleration phase, the saturation with fluid B remains unchanged (curve S1) and significant data concerning the characteristics of the porous material are lost.

The process according to the invention comprises keeping the sample in contact with the interface between two fluids such as it is outside the sample and thus at least at a minimum level. At this minimum level, the interface is flush with the base of the bar, i.e. at the furthest distance from the axis of rotation ($r_{max}$), at least during the deceleration phase.

According to a first implementing procedure, the displacement of the interface between the two fluids, outside the sample, is followed up as the denser fluid leaves the sample. In this case, the volume of the chamber inside bucket 2 must be large enough to receive all the fluid expelled from the sample.

Figure 1:
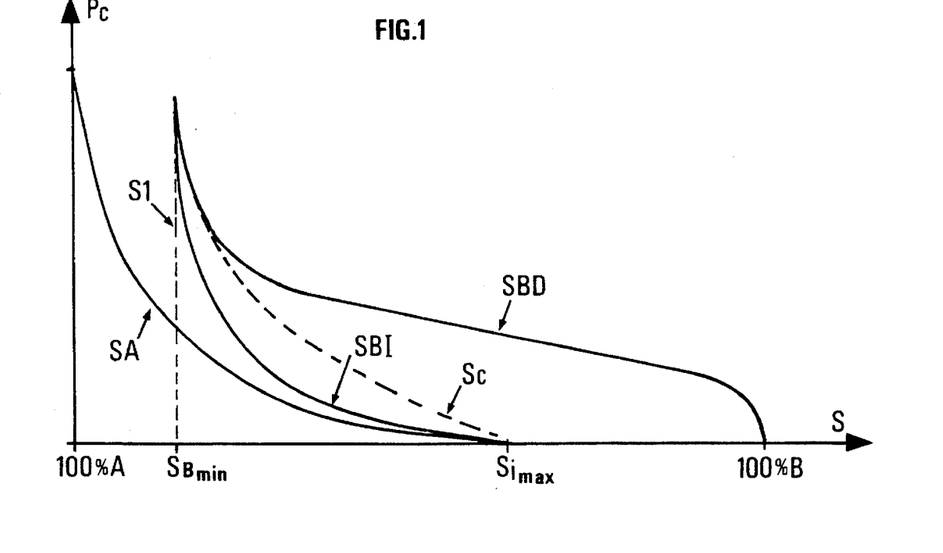
FIG. 1 shows curves representative of the variations in the saturation of a sample during a drainage-imbibition cycle.

Preferably, this flush level is kept as soon as it is reached during the previous draining phase, so as to preserve the continuity of the procedure. The process according to the invention therefore allows the imbibition of the porous material and therefore the measurement of the variations in the saturation with fluid B during the deceleration phase to be achieved. A phenomenon of hysterisis and a return along another variation curve (curve SBI) up to a relative maximum value $Si_{max}$ can be observed.

New draining-imbibition cycles may be achieved thereafter to study the evolution of saturations, the first one beginning with a draining phase along curve SC.

The process according to the invention may also be used to follow up the progressive saturation, with a fluid A, of a sample bar initially completely saturated with a fluid A at the maximum rotational speed, as this speed decreases (curve SA).

The process according to the invention is implemented (FIG. 2) by placing a sample bar 1 previously saturated with a fluid B such as salt water into a vessel or bucket 2 containing another fluid A such as oil. This vessel 2 is fastened to the end of an arm 3 which is rotated around an axis of rotation 4 at an increasing speed during a first draining phase, then at a decreasing speed during a second imbibition phase. The time when the position of the interface between the fluid B drained from the bar and the other fluid A reaches the level of the bar base is detected and, if necessary, this set level is maintained by transferring the excess fluid towards an auxiliary cavity.

Figures 2, 3:
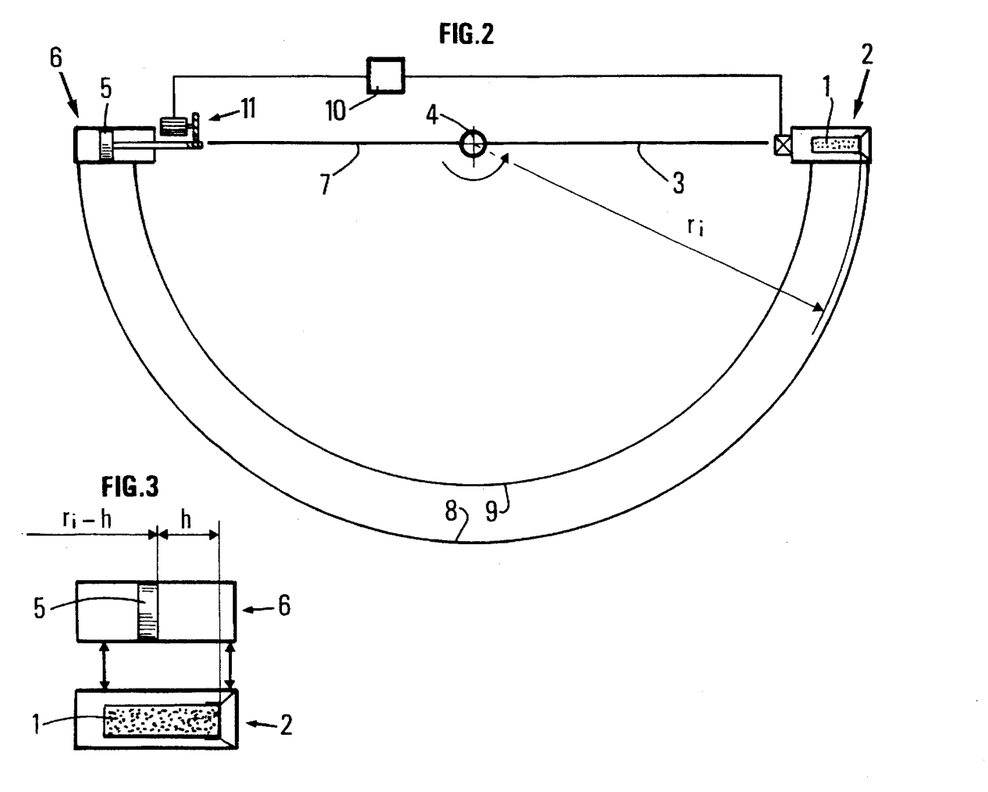
Figure 4:
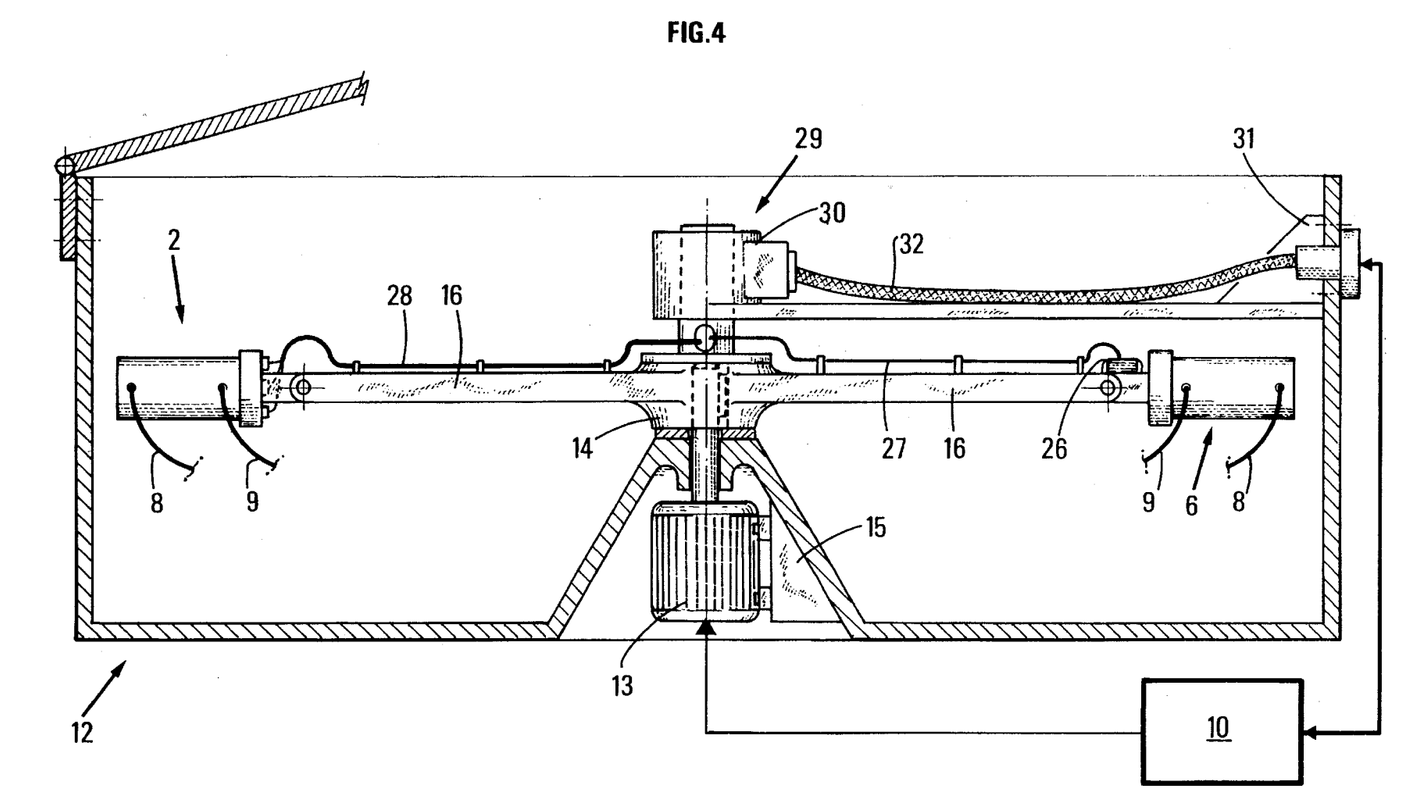
Figure 5:
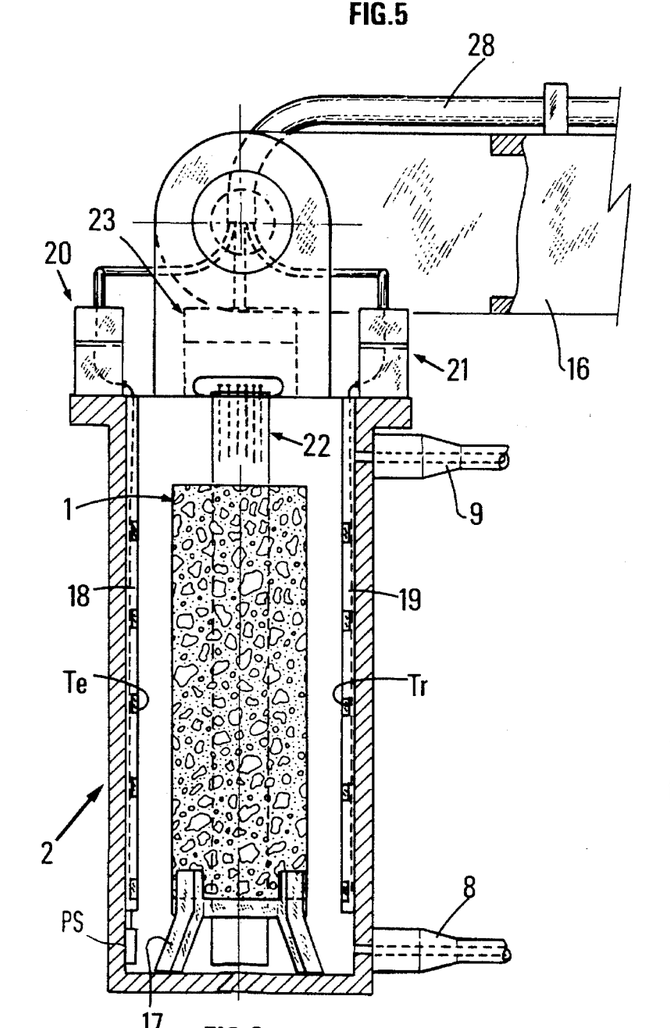
FIG. 5 is a cross-section of the lay-out of a bucket containing a sample.
Figure 6:
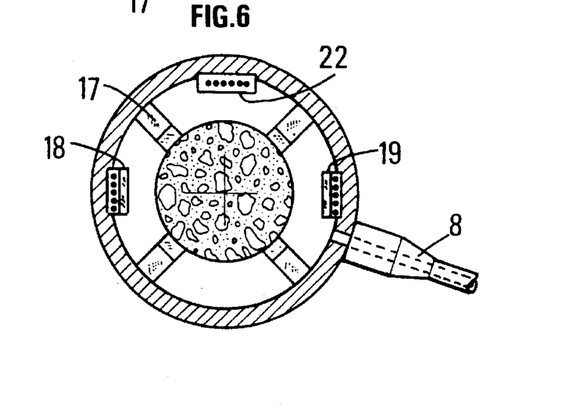
FIG. 6 shows the same bucket in cross-section.
Figure 7:
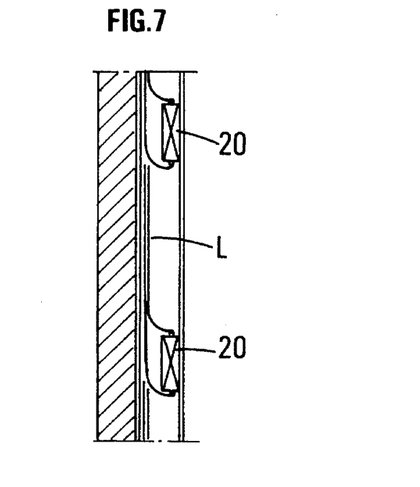
FIG. 7 shows a detail of an acoustic measuring rod.
Figure 8:
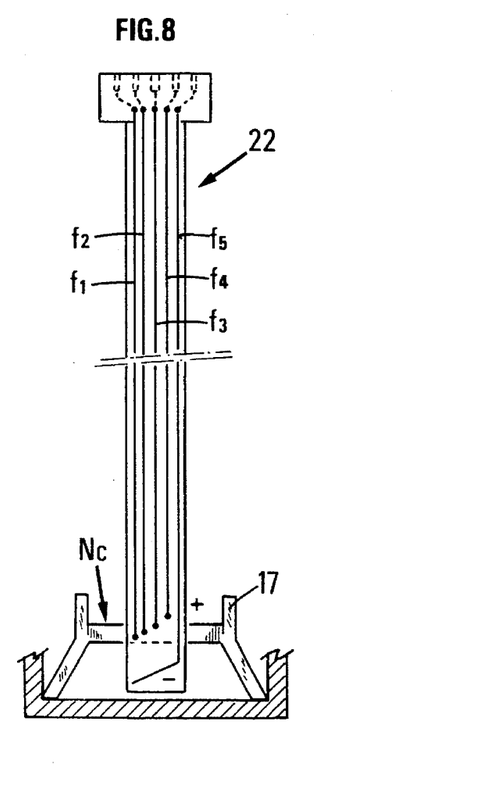
FIG. 8 shows an electric measuring means for measuring the level of the fluid expelled from a sample bar.
Figure 9:
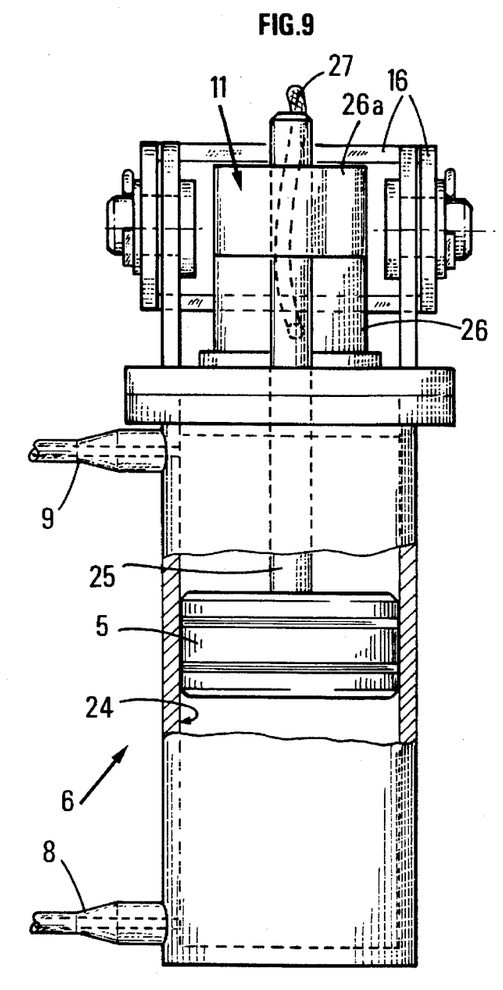
FIG. 9 is the cross-section of the lay-out of a displaceable-piston bucket.

According to one embodiment, this auxiliary cavity is delimited by a piston 5 mobile in another cylindric vessel 6 having substantially the same mass as the first one and similarly fastened to the end of an arm 7 substantially of equal length. The opposite sides of piston 5 communicate through flexible lines 8, 9 with the opposite ends of the first vessel.

A control system 10 connected to means for detecting the interface displacements, arranged in the first bucket or vessel 2, controls if need be motive means 11 adapted for moving the mobile piston 5. In an initial situation of equilibrium where no portion of fluid B leaves the bar, piston 5 is placed at the same distance ri (FIG. 2) as the set position between the two fluids A and B, so that the pressures on either side are balanced. At the end of the draining phase where the piston has been moved by a distance h to maintain the interface in the set position, the pressure difference between the pressures on either side of piston 5, which is expressed by:

$$dp = \rho \, \omega^2 h \, (ri-h),$$

remains very small in practice, of the order of a few hundred kPa. With this lay-out, motive means of relatively low power are sufficient in practice to move piston 5.

The practical embodiment of the device implementing the method, illustrated in FIGS. 4–9, includes in a tank 12 a centrifugation unit for centrifuging vessels or buckets. An electric motor 13 secured with the wall of tank 12 brings into rotation a hub 14 resting on a sole 15, provided with two arms 16 facing each other and substantially of equal length. The buckets such as 2, 6 are mounted pivoting at the ends of respectively the two arms 16 so as to be spontaneoulsy in line with the direction of the centrifugal force applied.

In the bucket 2 of cylindric shape for example, the bar to be tested is placed on a support 17. Acoustic means for detecting the displacements of the two fluids inside the bar are arranged in several determined places along the inner cavity of bucket 2, as described in patent application FR-2, 666,147 cited above. These means include two supporting rods 18, 19 arranged respectively in two diametrically opposite longitudinal grooves (FIG. 6) of the inner cavity. Piezoelectric chips Te, Tr, some of which are used as ultrasound transmitters, the others as ultrasound receivers, are respectively fastened along the two rods 18, 19 at regular intervals.

The electric conductors L associated with all the chips of each rod 18, 19 (FIG. 7) are connected, at one end thereof, respectively to electric connectors 20, 21. Each rod with its chips Te, Tr and the associated electric conductors is embedded in a protective resin.

By determining the time of propagation of impulses between the transmitter and the receiver of each couple, which varies according to whether the zone of the sample crossed thereby is more or less saturated with fluid A or B, the evolution of the interface may be followed up as the centrifugal force applied varies, as described in the French patent application cited above.

The device further comprises means for locating the level of the interface between the two fluids A and B.

According to a first embodiment which is suitable when the two fluids A and B have very distinct electric resistivities, the locating means are of the electric type. They include a rod 22 similar to rods 18, 19 on which several conducting wires of various lengths P1–PG are fastened in parallel. They may for example consist of tracks made of a noble metal and deposited on a platelet made of an insulating material. In the example schematized in FIG. 8, four tracks f1 to f4 of different lengths are used, whose lower ends are distributed on either side of the set level Nc to be complied with, the level of the bar base for example. The longitudinal spacing thereof is for example a few tenths of a millimeter. In operation, a potential difference is established between each of them and the fifth track f5. The five tracks are connected, at one end of rod 22, to an electric connector 23.

The bucket 6 fastened to the opposite arm 16 (FIG. 9) includes a cylindric cavity 24 in which piston 5 slides. The ends of bucket 6, on either side of piston 5, communicate with lines 8, 9. A stem 25 externally extended by a threaded part is fastened to piston 5. The motive means 11 for moving the piston include a motor 26 of the stepping motor type for example, supplied electrically by conductors 27 and a reduction box 26a coupled with the threaded stem 25.

The various conductors (FIG. 5) ending up at connectors 20, 21, 23 are connected to a bundle of conductors 28. Bundle 28 and the conductors 27 supplying motor 26 (FIG. 4) run alongside the two arms 16 up to a rotating connector 29 of a well-known type. The peripheral part 30 of this rotating connector is kept in position by a bracket 31 fastened to the wall of tank 12 and connected through a collecting cable 32 to the piloting system 10. The latter is adapted for:

controlling the motor 13 driving arms 16 during the draining and imbibition phases already described, measuring the variation in the position of the interface between the two fluids, controlling motor 26 according to the data permanently supplied by the electric detector 22, so as to stabilize, if necessary, the interface between the two fluids A, B at a predetermined set level, and controlling the acoustic telemetry cycles by means of the piezoelectric transducers of rods 18, 19.

The piloting system is for example a micro-computer of a well-known type provided with an interface card and programmed for synchronizing the various functions of control of the motors, of acquisition of the measuring data, of the interface height and, if need be, of regulation to a set level value.

Figure 10:
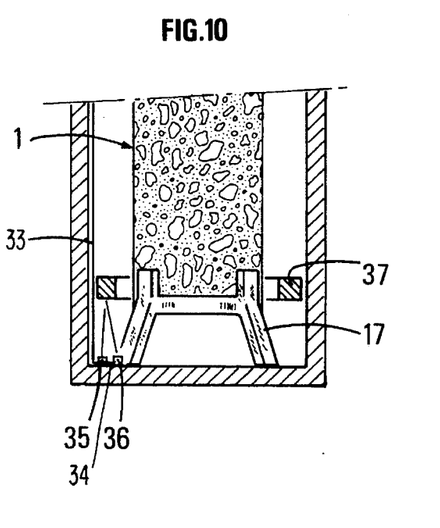
FIG. 10 is a partial cutaway view of a bucket provided with an electroacoustic means for detecting the level of the fluid expelled from a sample bar.

According to another embodiment, the means for locating the interface level is of the electro-acoustic type. In this case, rod 22, 23 is replaced by a rod 33 which may be inserted along the wall of the bucket and provided with a baseplate 34 for two piezoelectric chips 35, 36. Rod 33 is so positioned that the baseplate 34 is positioned on operation below the level of the expelled fluid, with the axes of chips 35, 36 directed towards the opposite end of bucket 2. A float 37 allowing the interface level to be followed up is arranged in the peripheral space around bar 1. One of the two chips is used for transmitting acoustic impulses, the other for receiving the echoes of the impulsions transmitted on the lower face of float 37. The rod similarly includes a longitudinal passageway for the conducting wires connecting chips 35, 36 to the piloting system 10 via bundle 28 (FIG. 4) and an electric connector such as 23. Like rods 18, 19, rod 33 is embedded in a protective resin.

This embodiment is advantageous in that the piloting system already includes an acoustic telemetry set associated with the piezoelectric chips 20, 21 (FIG. 5) and which may therefore carry out the measurements of the interface level. It is equally accurate since, in practice, level variations much less than 1/10th mm may be detected.

Without departing from the scope of the invention, a system provided with pressure detectors for measuring the position variations of the interface between the two fluids may be used instead of the previous acoustic telemetry system. Such a system includes a first pressure detector positioned so as to be submerged on operation in the expelled fluid. In order to compensate the measured pressure variations directly related to the variation of the centrifugal force, the opposite bucket 3 may be provided with a check pressure detector submerged in a fluid and the electric signals delivered by the two pressure detectors may be combined.

Figure 11:
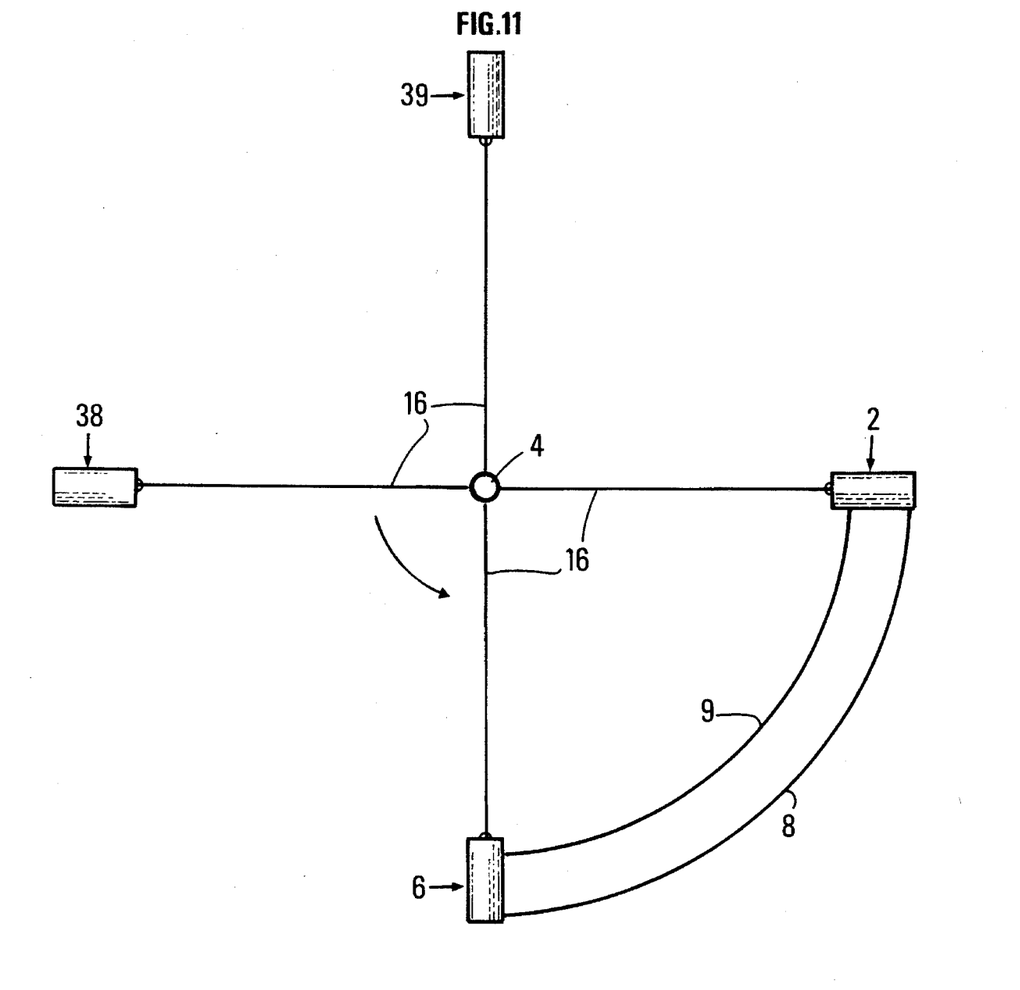
FIG. 11 shows another embodiment with a four-armed centrifuging rotary support.

The method may also be implemented by using a four-armed rotary support as schematized in FIG. 11, which generates a better balance in rotation and allows temperature compensations to be achieved. The two buckets 2 and 6 are arranged at the end of the two arms 16 at 90° with respect to each other. A sample bar having the same size as bar 1 is placed in a third bucket 38 similar to bucket 2. This bar is saturated with fluid and submerged therein. The telemetry measurements carried out by means of rods 18, 19 are used for the temperature balance of the analogous measurements obtained in bucket 6. The fourth bucket is used to balance bucket 3. It may further include a mobile piston such as 5, forced to follow the displacements imposed thereto by the piloting set, so as to obtain a better balance in rotation.

A device has been described in which the compensation cavity is arranged, for greater convenience, in a bucket 6 at the same distance from the axis of centrifugation as the bucket containing the sample bar. However, without departing from the scope of the invention, this cavity may be arranged in any other place, the main thing being to keep the interface between the two fluids at a predetermined set level and, in any case, in permanent contact with the sample.

Figure 12:
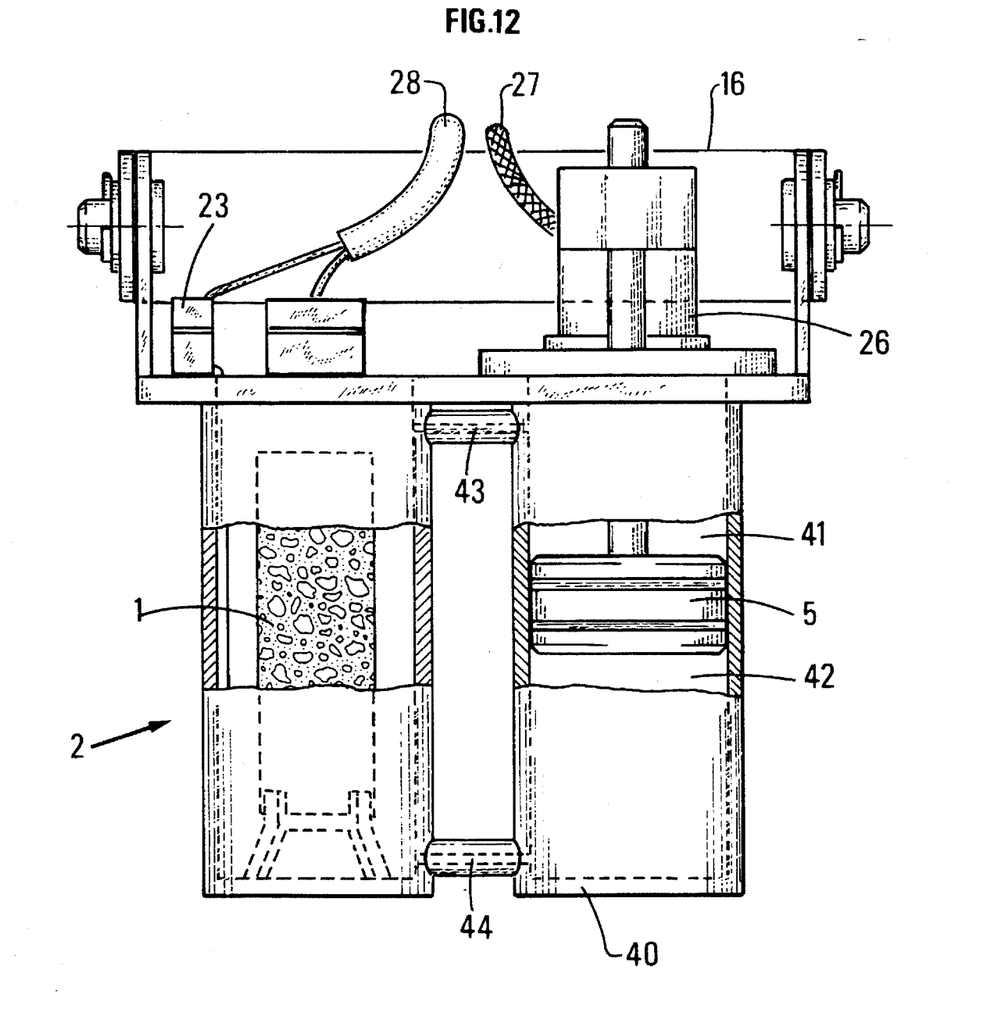
FIG. 12 shows another embodiment where the auxiliary chamber with the sliding piston and the inner cavity for the sample are in two side by side buckets communicating with each other.

As shown on FIG. 12 the auxiliary compensation chamber with the sliding piston 5 can also be placed in a vessel or bucket 40 pivotably mounted at the end of arm 16 by the side of bucket 2 containing the sample 1.

The cavities 41, 42 on opposite sides of the piston 5 communicate by channels 43, 44 respectively with the opposite end parts of the first bucket 2. Motor 26 is also controlled by the control system 10 (FIG. 4) for displacing piston 5 in the second bucket 40 thereby keeping the interface in contact with the sample 1.

It is clear that the two buckets 2, 40, can be replaced by a unique bucket provided with two cavities respectively for the sample 1 and the piston 5.

Keeping the interface constantly at the level of the bar base contributes to simplifying considerably the determination of the relative permeability coefficients which is performed for example by means of numerical simulations, as it is known to specialists. By keeping the interface level at the base of the bar, its length, which represents a limit condition imposed for calculations, may be considered constant during the process.

It is also possible to use the means for measuring the interface position, be they acoustic, electric or pressure measuring means, only to keep the sample in contact with the interface between the two fluids, and to let this interface move freely closer to the axis of rotation during the deceleration phase. It should be reminded that this implementation procedure allows the capillary pressure in the bar to be determined if the precise position of the interface is known.

We claim:

1. A process for surveying the properties of a permeable or porous material, which comprises applying a centrifugal force on a sample of material containing at least two fluids of different densities, the centrifugal force having a phase of growth up to a maximum value and then a phase of decrease, and measuring, as a function of the intensity of the centrifugal force applied, movement of the at least two fluids outside the sample, said process further comprises keeping the sample in permanent contact with the at least two fluids at least during the phase of decrease of the centrifugal force and measuring movement of at least one fluid of the at least two fluids reentering the sample and displacing another fluid of the at least two fluids as a function of said centrifugal force.

2. A process as claimed in claim 1, wherein measuring movement of the at least two fluids further comprises monitoring of an interface between said at least two fluids outside the sample during the phase of growth and the phase of decrease of the centrifugal force.

3. A process as claimed in claim 2, which further comprises maintaining said interface at a level of an outerface of the sample.

4. A process as claimed in claim 2, wherein the sample is an elongated bar oriented in the direction of the centrifugal force applied and which further comprises maintaining said interface at the level of a face of the sample through which fluid is expelled by the centrifugal force.

5. A process as claimed in claim 1, which further comprises maintaining an interface between said at least two fluids outside the sample at a predetermined set level.

6. A process as claimed in claim 5, wherein maintenance of the interface at a predetermined set level comprises detecting the level of the interface outside the sample by acoustic telemetry.

7. A process as claimed in claim 5, wherein maintenance of the interface at a predetermined set level comprises detecting the level of said interface outside the sample by electric conductivity.

8. A process as claimed in claim 5, wherein maintenance of the interface at a predetermined set level comprises detecting the level of said interface by pressure measurements in the at least two fluids outside the sample.

9. A process as claimed in claim 1, wherein said sample comprises a permeable or porous sample, which further comprises placing the permeable or porous sample containing at least the two fluids of different densities in a vessel provided with a cavity for collecting expelled fluid from the sample, applying said centrifugal force by rotating the vessel around an axis of rotation and transferring the fluids between the vessel and an auxiliary cavity to keep the sample substantially in contact with the at least two fluids and to maintain an interface between the at least two fluids at least at a level of a face of the sample located at a furthest distance from the axis of rotation.

10. A device for implementing the method as claimed in claim 1, which comprises at least a first vessel provided with an inner cavity for containing the sample in contact with the at least two fluids of different densities, the vessel being pivotally mounted to the end of a first arm integral with an axle, motor means for driving the arm in rotation and generating a centrifugal force, and means for monitoring displacements of the two fluids inside the sample, said apparatus further comprising a variable-volume auxiliary chamber communicating with the first vessel, means for determining the position of an interface between one fluid of the at least two fluids expelled by the centrifugal force and another fluid of the at least two fluids outside the sample, and a piloting system for controlling fluid transfer between said vessel and said auxiliary chamber to maintain said fluid interface at a set level and to avoid any loss of contact between the fluids and the sample.

11. A device as claimed in claim 10, further comprising a second vessel fastened to the end of a second arm integral with said axle, a piston adapted for tightly sliding into the second vessel and delimiting two chambers, one of said two chambers being said variable-volume auxiliary chamber, means for placing said two chambers, respectively, in communication with opposite end parts of said first vessel and second motor means controlled by said piloting system for moving the piston in the second vessel thereby maintaining said interface in contact with the sample.

12. A device as claimed in claim 11, comprising two other arms arranged so as to balance said axle and each provided with a vessel, one of said arms including electro-acoustic transducer means electrically connected to the piloting system for performing a temperature compensation, thereby allowing temperature drifts likely to affect a set of transducers of the first vessel to be corrected.

13. A device as claimed in claim 10, further comprising a second vessel fastened to the end of said first arm, a piston adapted for tightly sliding into said second vessel and delimiting two chambers, one of said two chambers being said variable-volume auxiliary chamber, means for placing said two chambers, respectively, in communication with the opposite end parts of said first vessel and second motor means controlled by said piloting system for moving the piston in said second vessel thereby maintaining said interface in contact with the sample.

14. A device as claimed in claim 10, wherein the means for monitoring the displacements of the fluids inside the sample include two sets of electro-acoustic transducer elements distributed inside the first vessel to determine the time of propagation of acoustic waves through said sample.

15. A device as claimed in claim 14, wherein the sets of transducers are arranged on supporting rods associated with means for electronically connecting the transducers to the piloting system.

16. A device as claimed in claim 10, wherein one of the at least two fluids is electrically conductive, said means for determining the location of the interface including conductive elements, each having one end arranged at a different level close to said level, these conductive elements being connected to an electric source by an electrical connector.

17. A device as claimed in claim 16, wherein the conductive elements are arranged on a supporting rod associated with means for electrical connection to the piloting system.

18. A device as claimed in claim 10, wherein said means for determining the location of the interface include acoustic echo sounding elements for determining the variations of the interface level.

19. A device as claimed in claim 10, wherein said means for determining the location of the interface include means for measuring pressure variations linked to the height variation of the denser fluid in said inner cavity.

* * * * *